United States Patent [19]

Olson

[11] 4,288,614

[45] Sep. 8, 1981

[54] PROCESS FOR THE PREPARATION OF ESTERS OF 5-FORMYL-3-METHYL-2,4-PENTADIEN-1-OL

[75] Inventor: Gary L. Olson, Westfield, N.J.

[73] Assignee: Hoffmann-La Roche Inc., Nutley, N.J.

[21] Appl. No.: 118,942

[22] Filed: Feb. 6, 1980

Related U.S. Application Data

[62] Division of Ser. No. 9,218, Feb. 5, 1979, Pat. No. 4,222,943, which is a division of Ser. No. 772,711, Feb. 28, 1977, Pat. No. 4,152,520, which is a division of Ser. No. 594,386, Jul. 9, 1975, abandoned.

[51] Int. Cl.$^3$ .............................................. C07C 67/24
[52] U.S. Cl. .............................. 560/240; 260/345.7 R; 260/345.8 R; 546/268
[58] Field of Search .................................. 560/240

[56] References Cited

U.S. PATENT DOCUMENTS

| | | | |
|---|---|---|---|
| 3,622,586 | 11/1971 | Jezie | 546/268 |
| 3,760,004 | 9/1973 | Freyerschlag et al. | 568/459 |
| 3,875,174 | 4/1975 | Edwards | 546/268 |

FOREIGN PATENT DOCUMENTS 1275050  8/1968  Fed. Rep. of Germany.

OTHER PUBLICATIONS

Shavrygina et al., J. Org. Chem. USSR 2, 1349–1351, (1966).
Konowal et al., Rocz. Chem. 42, 2045–2059, (1968).
Makin, Russ. Chem. Rev., 38, 237–248, (1969).
Zwierzchowska-Nowakowska et al., Rocz. Chem. 48, 1929–1940, (1974).
Woods et al., J. Am. Chem. Soc., 68, 2483–2485, (1946).
Houben-Weyl, Methoden der Organischen Chemie, vol. VII/1, p. 249, (1954).
Pommer, Angew Chem. 72, pp. 811–819, (1960).
Jurczak et al., Rocz. Chem. 44, pp. 1587–1590, (1970).
Chmielewski et al., Rocz. Chem. 46, pp. 627–631, (1972).

Primary Examiner—Natalie Trousof
Assistant Examiner—Vera C. Clarke
Attorney, Agent, or Firm—Jon S. Saxe; Bernard S. Leon; George W. Johnston

[57] ABSTRACT

A novel process for the preparation of esters of 5-formyl-3-methyl-2,4-pentadien-1-ol which employs as starting materials 2-substituted-3-methyl-6-alkoxy-3,6-dihydro-2H-pyrans. Novel intermediates are also disclosed.

3 Claims, No Drawings

PROCESS FOR THE PREPARATION OF ESTERS OF 5-FORMYL-3-METHYL-2,4-PENTADIEN-1-OL

This is a division of application Ser. No. 9,218, filed Feb. 5, 1979, now U.S. Pat. No. 4,222,943, which in turn is a division application of Ser. No. 772,711, filed Feb. 28, 1977, now U.S. Pat. No. 4,152,520, which in turn is a division application of Ser. No. 594,386, filed July 9, 1975, now abandoned.

BACKGROUND OF THE INVENTION

This invention is directed to the preparation of esters of 5-formyl-3-methyl-2,4-pentadien-1-ol. This bifunctional molecule is an important intermediate in the synthesis of vitamin A particularly by Wittig condensation with an ionyl phosphonium salt (Pommer, *Angew Chem.*, 72, 811 (1960). This diene has previously been prepared by uneconomic procedures requiring multistep operations (Pommer, Ibid.). The procedure disclosed and claimed herein provides a simple and direct alternative to prepare the bifunctional diene of interest. The instant process employs as starting materials 2-substituted-3-methyl-6-alkoxy-3,6-dihydro-2H-pyrans, which are products of the Diels-Alder reaction of 1-alkoxy-1,3-pentadiene and heterodienophiles.

The preparation of 2-substituted-3-methyl-6-alkoxy-3,6-dihydro-2H-pyrans by the Diels-Alder condensation of 1-ethoxy-1,3-pentadiene with ethyl glyoxylate, chloral and formaldehyde has been reported previously in the literature (Shavrygina et al., *J. Org. Chem.* USSR, 2, 1394 (1966). Other Diels-Alder condensations of 1-alkoxydienes with esters of glyoxylic acid have been reported by Konowal et al. *Rocz. Chem.*, 42, 2045 (1966) and by Makin, *Russ Chem. Rev.*, 38, 237 (1969). An extensive series of articles has been published on the use of 2-substituted-6-alkoxy-3,6-dihydro-2H-pyrans as starting materials for the synthesis of monosaccharides. Among such articles are Chimelewski et al., *Rocz Chem.*, 46, 627 (1972), Zwierzchowska-Nowakowska et al., *Rocz Chem.*, 44, 1587 (1970).

In addition to the above mentioned studies with 1-alkoxy-dienes, Zwierzchowska-Nowakowska et al., *Rocz Chem.*, 48, 1928 (1974), describes the Diels-Alder condensation of 1-acetoxy-1,3-butadiene with butyl glyoxylate to form acetoxy substituted 2H-dihydropyrans.

Hydrolysis of 2-substituted-6-alkoxy-3,6-dihydro-2H-pyrans in the presence of phenylsemicarbazide reagent to afford delta-hydroxy-alpha, beta-unsaturated aldehyde semicarbazones has been described by Shavrygina et al. (supra) and the reaction of 1-methoxy-3,6-dihydro-2H-pyran to afford penta-1,3-dien-1-al during the course of steam distillation from phosphoric acid has been described by Woods and Sanders, *J. Am. Chem. Soc.*, 68, 2483 (1946).

The dealcoholation and isomerization of 2-substituted 6-alkoxy-3,6-dihydro-2H-pyrans to form 1-substituted-5-formyl-1,3-pentadienes has been unknown heretofore.

The instant invention provides the art with a novel, efficient and economical method of preparing esters of 1-hydroxy-5-formyl-3-methyl-2,4-pentadiene.

SUMMARY OF THE INVENTION

This invention is directed to the preparation of a compound having the formula:

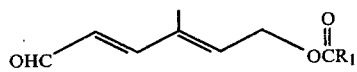

wherein $R_1$ is lower alkyl;
which comprises treating a compound of the formula:

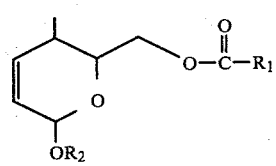

wherein $R_1$ is as defined above and $R_2$ is lower alkyl; under dealcoholation conditions in the presence of an isomerization catalyst.

DETAILED DESCRIPTION OF THE INVENTION

The term "lower alkyl", as used herein, denotes straight or branched chain saturated hydrocarbon groups of 1 to 6 carbon atoms, for example, methyl, ethyl, propyl, butyl and the like. As further used herein, the term "lower alkoxy" denotes alkoxy groups having 1 to 6 carbon atoms such as, for example, methoxy, ethoxy, propoxy and the like. The term "lower alkylene" as used herein, denotes straight or branched chain aliphatic hydro carbon groups having 1 to 6 carbon atoms such as methylene, ethylene, butylene, isobutylene and the like. The term "lower acyl" as used herein, denotes acyl groups having from 1 to 6 carbon atoms such as formyl, acetyl, and propionyl. The term "halogen", as used herein, denotes chlorine, bromine, iodine and fluorine. The term "lower alkanol" as used herein, denotes straight or branched chain alkanols having from 1 to 6 carbon atoms such as methanol, ethanol, isopropanol, butanol and the like. The term "aryl" as used herein, denotes unsubstituted mono or polynuclear aryl groups such as phenyl, naphthyl, anthryl, phenanthryl and the like. The term "aryl lower alkyl" as used herein, denotes aryl alkyl groups wherein the aryl and alkyl moieties are as defined above. The term "lower acyloxy" denotes acyloxy groups having 1 to 6 carbon atoms such as formyloxy, acetoxy and propionyloxy. The term "lower alkyl aryl", as used herein denotes alkyl aryl groups wherein the alkyl and aryl moieties are as defined above.

Compound I may be prepared in accordance with the following reaction scheme:

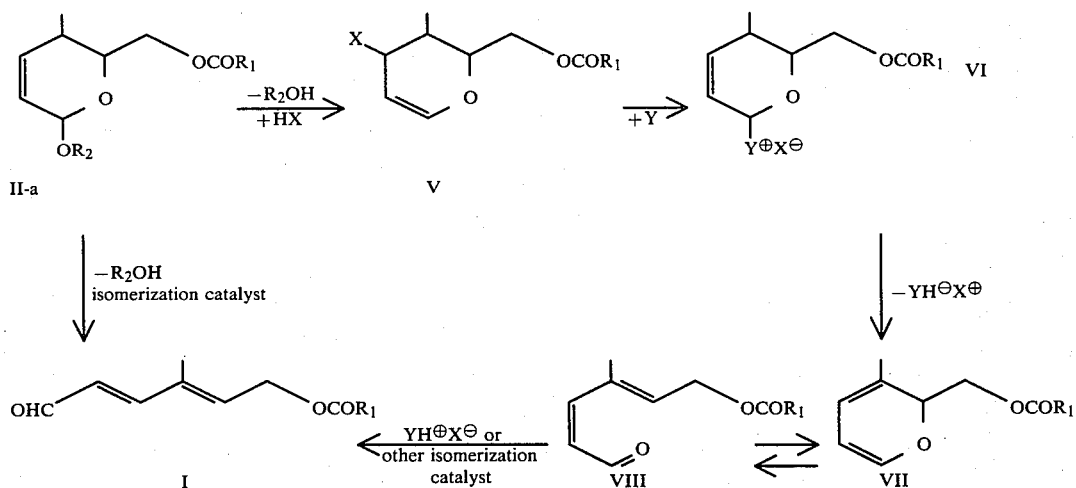

wherein X is halogen and Y is an amine selected from the group consisting of ammonia, lower alkyl aliphatic amines, aromatic amines, and heterocyclic amines.

The initial step in the preparation of the compound of formula I involves the formation of a compound having the following formula:

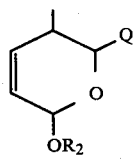

II wherein $R_2$ is defined above; Q is formyl,

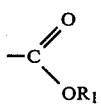

where $R_1$ is as previously defined;
—$CH_2OH$, —$CH_2OR_5$ where $R_5$ is lower acyl;
which comprises reacting a compound having the formula:

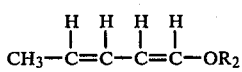

III wherein $R_2$ is as previously defined;
with a compound having the formula:

IV wherein Q is as defined above.

The above reaction between compounds III and IV to form compound II may be conducted in the presence or absence of solvent at temperatures varying from about $-15°$ C. to about $+200°$ C. If it is desired to employ a solvent, any inert organic solvent may be used. Typical solvents that may be employed are aliphatic hydrocarbons such as pentane, hexane, heptane, octane and the like; aromatic hydrocarbons such as benzene, xylene, toluene, naphthalene and the like; halogenated hydrocarbons such as methylene chloride, carbon tetrachloride, chlorobenzene and the like; amides such as formamide, dimethylformamide (DMF), tetramethylurea, hexamethylphosphoric acid triamide; ethers such as dioxane, anisole and tetrahydrofuran; nitriles such as acetonitrile, benzonitrile and the like; ketones such as acetone, cyclohexanone and the like. Solvents such as dimethylsulfoxide (DMSO) and N-methylpyrrolidone may also be employed. The above-mentioned solvents may be used singly or in combination.

A preferred starting material for the preparation of compound I, is a compound having the formula:

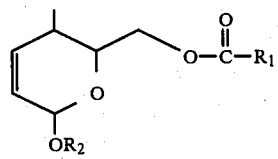

II-a wherein $R_1$ and $R_2$ are as previously defined.

A particularly preferred starting material in accordance with compound II-a is when $R_2$ is ethyl and $R_1$ is methyl. Compound II-a is novel and forms one aspect of this invention.

Generally, compound II-a may be formed by reduction of the compound of formula II where Q is

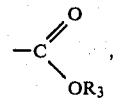

wherein $R_3$ is lower alkyl with a chemical reducing agent useful for the conversion of esters to alcohols, such as lithium aluminum hydride, sodium aluminum hydride, diisobutyl aluminum hydride and the like, followed by acetylation of the alcohol produced in the reduction, a compound of the formula II where Q=$CH_2OH$, with any conventional acetylation agent. Exemplary of the acetylation agents that may be used are compounds such as acetic anhydride-pyridine, benzoyl chloride-triethylamine and the like.

Specifically, a preferred embodiment of compound II-a is prepared by reacting 1-ethoxy-1,3-pentadiene with n-butyl glyoxylate in accordance with the procedures described hereinbefore. The reaction product is a compound having the formula of compound II wherein Q is

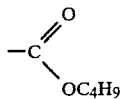

Compound II-a may then be formed by reduction and acetylation as set forth hereinabove. The formation of compound II-a may be carried out in the presence or absence of solvent. If a solvent is employed, said solvent may be selected from those mentioned hereinbefore. Although the butyl ester has been specifically described, the process is not limited thereto.

Alternatively, compound II-a may be formed in accordance with the above procedure by reacting 1-ethoxy-1,3-pentadiene with glyoxal to yield a compound of formula II where Q is formyl. Compound II-a is formed by reduction with the chemical reducing agents set forth hereinbefore and with other reducing agents, e.g., sodium borohydride, suitable for the reduction of aldehydes to alcohols and acetylation in accordance with the procedures set forth hereinbefore.

When Q in compound II is —$CH_2OH$, the formation of compound II-A is formed simply by acetylation as previously described.

Compound II-a may then be converted to the compound of formula I by dealcoholation in the presence of an isomerization catalyst as set forth in the reaction scheme.

The dealcoholation of compound II-a may be effected in a stepwise manner in accordance with the scheme set forth hereinbefore whereby compound II-a is transformed to a compound of the formula:

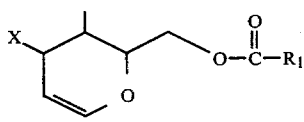

wherein $R_1$ and X are as previously defined;
by treatment of the former with a conventional halogenating agent.

Compound V is novel and forms another aspect of this invention.

Typical halogenating agents that may be employed are thionyl chloride, $PX_3$, $PX_5$, HX, $CH_3C_6H_4SO_2X$, $COX_2$ (where X is halogen) and the like. The preferred halogen is chlorine. The halogenation is carried out at temperatures ranging from about 15° C. to about 200° C. Solvents that may be employed for the reaction are those mentioned hereinbefore. Diethyl ether and carbon tetrachloride with HCl or $SOCl_2$ may also be employed. HCL in diethyl ether or thionyl chloride in $CCl_4$ is particularly preferred.

Compound V is then transformed to a compound of the formula:

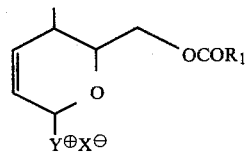

wherein $R_1$, X and Y are as defined above.

Compound VI is novel and forms yet another aspect of this invention. Compound V may then be transformed to compound VI by treating compound V with an amine. Typical amines that may be employed are ammonia, aliphatic amines such as lower alkyl primary, secondary and tertiary amines. Typical aliphatic amines that may be used are methylamine, diethylamine, triethylamine and the like. Aromatic amines such as aniline, o-toluidine may also be employed. Heterocyclic amines such as pyridine are also usable in this procedure. Pyridine is preferred. The reaction is carried out at a temperature ranging from about 0° C. to about 50° C., preferably about 25° C.

Compound VI is then transformed to a reaction product consisting of a compound of the formula:

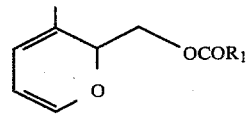

and a compound of the formula:

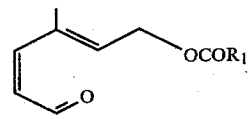

wherein $R_1$ is as previously defined.

Compound VII is novel and forms an additional aspect of this invention. Compound VII is obtained by heating a solution of compound VI at a temperature of from about 75° C. to about 150° C., preferably about 90° C. The transformation of compound VI to VII results in the elimination of the YH⊕X⊖ moiety from compound VI. The solvent employed to carry out this transformation may be any of those mentioned hereinbefore. Particularly preferred are either DMF in toluene or N-methyl pyrrolidinone. The transformation of VI to VII may be effected in situ immediately following the transformation of compound V to compound VI. If compound VI has been isolated and stored, it may then be dissolved and heated as described hereinbefore to form compound VII. If the reaction of compound V with an amine is carried out at a temperature of about 75° C. to about 150° C., preferably about 90° C., in one of the aforementioned solvents, the in situ transformation proceeds to afford compound VII without isolation of compound VI.

The reaction product consisting of compound VII which is in tautomeric equilibrium with compound VIII is then transformed to the compound of formula I by isomerization. The isomerization catalyst may be the eliminated YH⊕X⊖ moiety from the transformation of compound VI to VII or it may be an externally added catalyst. Compounds which may be employed as isomerization catalysts are lower alkyl and lower alkyl aryl and aryl sulfonic acids such as benzenesulfonic acid, methanesulfonic acid and p-toluenesulfonic acid; lower alkyl carboxylic acids such as formic and acetic acids; lower alkyl dicarboxylic acids, such as oxalic acid, may also be employed. Halogenated lower alkyl carboxylic acids such as di- and trihalo acetic acids, e.g., trichloroacetic acids, are also usable herein. Acid salts of amine bases, such as ammonium halides, hydrohalides of heterocyclic amines, particularly pyridine hydrochloride, lower alkyl amine acid salts such as the hydrohalides of triethylamine, aniline, o-toluidine and the like, may also be used. In addition, organo metallic compounds and other compounds of group VIII metals which are well-known olefin isomerization catalysts, e.g., $PdCl_2$, may be used. Pyridine hydrochloride is particularly preferred.

When the transformation of compound II-a to compound I is carried out utilizing an amine hydrohalide, especially pyridine hydrochloride, the hydrohalide acts as a dealcoholating agent affording the halide, compound V, which is immediately converted by the amine to the compound VI. If the reaction is carried out at temperatures in the range of 80° C. to 200° C., preferably 120°–150° C., the compound VI liberates the amine hydrohalide unchanged and compound VII is formed. At these temperatures, the liberated amine hydrohalide acts as a catalyst for the isomerization of the reaction product consisting of a mixture of compound VII and compound VIII to the compound of formula I. Thus, while the reaction of II-a proceeds via compounds V, VI, VII and VIII, the transformation of compound II-a to compound I is effected directly.

Since the amine hydrohalide is unchanged in the transformation of compound II-a to compound I, it is a catalyst and may be used in non-stoichiometric amounts. For example, it may be used in amounts from about 0.1 mole % to about 10 mole %, particularly 2.5 mole % to about 10 mole %. Amounts up to and in excess of 100 mole % may be employed without seriously altering the reaction, although no particular benefits are gained thereby.

The amine hydrohalides which can be used are those mentioned hereinbefore, pyridine hydrochloride being especially preferred. The solvents that may be employed are those mentioned hereinbefore with DMF and N-methyl pyrrolidinone being especially preferred.

In accordance with the aforementioned scheme, compound II-a may be transformed directly to compound I by treating compound II-a with an agent which acts both as a dealcoholation agent and an isomerization catalyst. The compounds which may be employed as dealcoholation/isomerization agents are those compounds set forth hereinbefore that effect the transformation of compound VIII to compound I.

Mixtures of lower alkyl carboxylic acids and their anhydrides, such as acetic acid-acetic anhydride may be employed as well. Other acidic catalysts include $CuSO_4$ and $KHSO_4$. Lewis acids, such as aluminum chloride, aluminum bromide, boron trifluoride, ferric chloride, stannic chloride, zinc chloride and the like may also be employed. Particularly preferred is aluminum chloride. The reaction is carried out in a solvent at temperatures varying from about 75° C. to 150° C. Typical solvents that may be employed are aliphatic hydrocarbons such as hexane, heptane, octane; aromatic hydrocarbons such as benzene, toluene and xylene. Solvents such as sulfolane, nitromethane and acetonitrile may also be used. These solvents may be used singly or in admixture. A preferred solvent is benzene.

The following non-limiting examples serve to illustrate the instant invention. All temperatures are in degrees centigrade.

EXAMPLE 1

Preparation of butyl 3-methyl-6-alkoxy-3,6-dihydro-2H-pyran-2-carboxylate

The general procedure was as follows:

A mixture of an alkoxypentadiene, butyl glyoxylate, and hydroquinone or a solution of these compounds in methylene chloride was stirred at the indicated temperature for the time given in Table I. The solvent where present was removed by distillation at atmospheric pressure. Further distillation at reduced pressure through Vigreaux column gave a complete separation of the starting materials and product 2H-pyran butyl ester in the yields indicated in Table I.

TABLE I

| 1-alkoxy pentadiene (mmole) | n-butyl glyoxylate (mmole) | Temperature | Time | Solvent[a] | Recovered Starting Materials | Yield[c] |
|---|---|---|---|---|---|---|
| 1-methoxy pentadiene 38.5 | 77.0 | 105° | 9 hr | — | — | 55% |
| 1-ethoxy pentadiene 28.0 | 26.4 | 100–105° | 18.5 hr | — | 1.83 g. | 46% |
| 1-ethoxy pentadiene 28.0 | 26.4 | reflux | 47 hr | $CH_2Cl_2$ | 3.81 g. | 36% |
| 1-ethoxy pentadiene 29.0 | 32.2 | 120° | 4.5 hr | — | 1.42 g. | 40% |
| 1-ethoxy pentadiene 226 | 250 | reflux | 48 hr | $CH_2Cl_2$ | 28.0 g. | 34% |

[a]hydroquinone was added to all reaction mixtures
[b]a mixture of diene and butyl glyoxylate
[c]based on limiting reagent.

EXAMPLE 2

Following the procedure of Example 1, with the exception that glyoxal in lieu of butyl glyoxalate is reacted with the 1-ethoxy-1,3-pentadiene, 3,6-dihydro-3-methyl-6-ethoxy-2H-pyran-2-carboxaldehyde is prepared.

To a solution of 0.505 g. (2.76 mmol) of the 2H-pyran aldehyde (purity 93% by gc) in 5 ml. of ethanol was added 0.056 g. (1.47 mmol) of sodium borohydride. The mixture was stirred for 1.5 hour at room temperature, cooled for 0°, and the excess sodium borohydride was destroyed by the addition of 1.4 mmol of acetone. The mixture was then concentrated to a volume of 1.4 ml., poured into water and extracted with two portions of ether. The ether extracts were washed with two portions of water, brine, dried (Na₂SO₄) and concentrated to give 0.258 g. (54%) of 3-methyl-6-ethoxy-3,6-dihydro-2H-pyran-2-methanol. All aqueous phases from the extraction procedure were reextracted with two portions of ether, and the ether extracts were washed with brine. The brine was extracted with ether and the combined ether solutions were dried (Na₂SO₄) and concentrated to give an additional 0.187 g. (39%) of 2H-pyran alcohol. The two concentrates were combined to give 0.445 g. (93%) of the 2H-pyran alcohol as a colorless oil.

EXAMPLE 3

This example illustrates the reduction of 3-methyl-6-ethoxy-3,6-dihydro-2H-pyran-2-carboxylate, butyl ester to the corresponding alcohol.

To a suspension of 1.90 g. (0.050 mol) of lithium aluminum hydride in 100 ml. of ether at 0°–5°, was added over 30 minutes a solution of 18.63 g. (0.071 mol) (purity 92% by gc). The mixture was stirred for 2 hours at 0° and 30 ml. of saturated magnesium sulfate solution was added, followed by solid magnesium sulfate. The mixture was then filtered and the filtrate was washed with 150 ml. of water. The water was extracted with 75 ml. of ether and the combined ether solutions were washed with 75 ml. of brine, dried (MgSO₄) and concentrated to give 13.31 g. (109%) of 3-methyl-6-ethoxy-3,6-dihydro-2H-pyran-2-methanol as a colorless liquid.

To a solution of 12.10 g. of crude 2H-pyran alcohol in 106 ml. of hexane and 16.1 g. (0.159 mol) of triethylamine was added 20.7 g. (0.203 mol ) of acetic anhydride dropwise at room temperature over 15 minutes. The mixture was stirred for 16 hours and poured into 300 ml. of saturated sodium bicarbonate solution and ice (total volume 500 ml.), stirred for 1 hour, and extracted with two 100-ml. portions of ether. The ether extracts were washed with 50 ml. of saturated cupric sulfate solution and with three 150-ml. portions of brine, dried (MgSO₄) and concentrated to give 14.02 g. (93%) of crude 2H-pyran acetate. Distillation of the crude 2H-pyran, (14.02 g. plus 1.1 g. prepared in the same manner from 1.0 g. of crude alcohol) afforded 10.11 g. of pure 3-methyl-3,6-dihydro-2H-pyran-2-methanol. Yield based on butyl ester, 66%.

Anal. calcd. for $C_{11}H_{18}O_4$: C 61.66, H 8.47. Found: C 61.97, H 8.64.

EXAMPLE 4

Preparation of 3-methyl-4-chloro-3,4-dihydro-2H-pyran-2-methanol acetate (chloroenol ether)

To a solution of 0.113 g. (0.53 mmol) of 3-methyl-6-ethoxy-3,6-dihydro-2H-pyran-2-methanol acetate in 2 ml. of ether at 0° was added 0.12 g. (1.0 mmol) of thionyl chloride. The mixture was stirred at 0° for 1 hour, at room temperature for 4.75 hours and concentrated to give 0.098 g. (103%) of the crude chloroenol-ether as a colorless oil (ca. 70% pure by nmr).

EXAMPLE 5

Preparation of 6-acetoxy-hexa-2,4-dien-1-al

The general procedure was as follows:

To a solution of 3-methyl-6-ethoxy-3,6-dihydro-2H-pyran-2-methanol acetate in the reaction solvent was added a solution of the catalyst or the anhydrous solid. The reaction mixture was placed into a preheated bath at the indicated temperature and stirred for the given time. It was then cooled, filtered in the case of insoluble catalysts, poured into a saturated sodium bicarbonate solution and extracted with organic solvent. The organic extracts were washed with brine, dried (Na₂SO₄) and concentrated to give the crude product. The reaction conditions and yields are given in Table II.

TABLE II

| 2H-Pyran (mmole) | Catalyst (mole %) | Solvent (ml) | Temp. °C. | Time hr. | Yield C₇ Aldehyde |
|---|---|---|---|---|---|
| 1.21 | AcOH<br>AC₂O<br>NaOAc | 1.0 ml<br>0.5 ml<br>0.19 g | 110°–120° | 2 | 10.6 |
| 0.47 | CH₃SO₃H | 1.0 xylene | 120° and reflux (140°) | 0.5<br>1.25 | 4.2 |
| 0.23 | KHSO₄ | 160.0 xylene | reflux | 0.33 | 9.1 |
| 0.23 | CuSO₄ | 108.0 xylene | reflux | 0.4 | 2.0 |
| 0.53 | AlCl₃ | 6.0 xylene | reflux | 2.25 | 17.0 |
| 0.88 | pyr . HCl | 38.0 DMF | 90° | 0.5 | 65.0 |

The following examples illustrate the preparation of 6-acetoxy-hexa-2,4-dien-1-al from the compound of Example 4.

EXAMPLE 6

A sample of the chloroenol ether of Example 4 (crude, 0.06 g., 0.29 mmol) was dissolved in 0.4 ml. of pyridine-d₅ in an nmr tube and the spectrum was run after the following periods; 1 hour at room temperature, 30 minutes at 50°, 1 hour at 95°. An immediate decrease in the vinyl proton doublet at δ6.40 ppm and appearance of vinyl proton multiplets at 5.6–6.1 ppm (pyridine HCl salt of the chloroenol ether) was observed along with the splitting of the acetate methyl into two peaks at 2.00 and 2.07 ppm. After warming to 95° for 1 hour, the nmr showed the product to be a mixture of 6-acetoxy-hexa-2,4-dien-1-al and unreacted 3-methyl-6-ethoxy-3,6-dihydro-2H-pyran-2-methanol acetate carried through as a contaminant in the chloroenol ether.

In a separate experiment, 0.08 g. (0.39 mmol) of the crude chloroenol ether was treated with 1.0 ml. of anhydrous pyridine at room temperature for 15 minutes. Evaporation of the pyridine in vacuo gave the pyridine.HCl salt as an oil insoluble in benzene, carbon tetrachloride, or ether. Dissolution of the salt in chloroform and washing with water extracted 0.06 g. of the salt from the chloroform solution. Injection of a deuteriochloroform solution of the salt into a gas chromatograph resulted in thermal elimination to give the cis and trans isomers of the 6-acetoxy-hexa-2,4-dien-1-al and 3-methyl-2H-pyran-2-methanol acetate.

EXAMPLE 7

To a solution of 1.00 g. (4.67 mmol) of 3-methyl-6-ethoxy-3,6-dihydro-2H-pyran-2-methanol acetate in 10 ml. of ether was added 0.67 ml (9.34 mmol) of thionyl chloride, and the mixture was refluxed for 6.5 hours. The reaction mixture was concentrated to a pale yellow oil which was dissolved in 10 ml. DMF and was treated with 0.55 g. (7.00 mmol) of pyridine. This mixture was stirred at 90° for 35 minutes, cooled, poured into 40 ml. of water, extracted with three 25 ml. portions of toluene, and the toluene solution was washed with 10 ml. of saturated cupric sulfate solution, 50 ml. of water, 40 ml. of saturated sodium bicarbonate solution and 50 ml. of brine. The toluene solution was dried (Na₂SO₄) and concentrated to give 0.693 g. (88%) of the crude 6-acetoxy-hexa-2,4-dien-1-al as a yellow solid.

EXAMPLE 8

Preparation of 6-acetoxy-hexa-2,4-dien-1-al

The general procedure was as folows:

To a solution of 3-methyl-6-ethoxy-3,6-dihydro-2H-pyran-2-methanol acetate in the reaction solvent was added a solution of the catalyst or the anhydrous solid. The reaction mixture was placed into a preheated bath at the indicated temperature and stirred for the given time. It was then cooled, poured into water and extracted with an organic solvent. The organic extracts were washed with saturated sodium bicarbonate solution, water and brine, dried (Na₂SO₄) and concentrated to give the crude product. The reaction conditions and yields are given in Table III.

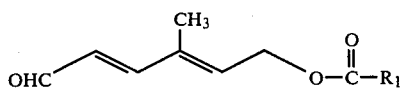

wherein $R_1$ is lower alkyl;
which comprises treating a compound of the formula:

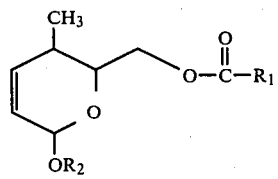

wherein $R_1$ is as above and $R_2$ is lower alkyl, with a catalytic amount of an amine hydrohalide at a temperature of from about 80° C. to about 200° C., said treatment being conducted in a polar aprotic solvent.

2. The process according to claim 1 wherein said amine hydrohalide is pyridine hydrochloride, said solvent is selected from the group consisting of dimethylformamide, dimethylacetamide and N-methyl pyrrolidinone, said process being conducted at a temperature of from about 120° C. to about 150° C.

3. The process according to claim 2 wherein the amount of said pyridine hydrochloride ranges from about 2.5 mole % to about 10 mole % and the solvent is N-methyl pyrrolidinone.

TABLE III

| Catalyst (mole %) | 2H-Pyran (mmole) | Conc. (mg/ml) | Solvent | Temp. (°C.) | Time (min) | Yield C₇ Aldehyde % |
|---|---|---|---|---|---|---|
| pyridine·HCl (NHCl) | 0.96 | 90 | DMF | 120 | 15 | 64 |
| 2.5 | | | | | | |
| 5.0 | 0.98 | 80 | " | 110 | 30 | 65 |
| 5.0 | 1.00 | 90 | " | 120 | 35 | 60 |
| 38.0 | 0.88 | 90 | " | 90 | 30 | 64 |
| 100.0 | 0.97 | 90 | " | 80 | 105 | 74 |
| 100.0 | 1.02 | 90 | " | 90 | 35 | 75 |
| 5.0 | 4.80 | 200 | N-methylpyrrolidinone | 130 | 9 | 71 |
| 5.0 | 0.98 | 90 | " | 150 | 1.75 | 76 |
| 10.0 | 1.43 | 150 | " | 90–93 | 150 | 73 |
| 10.0 | 1.46 | 150 | " | 110 | 35 | 72 |
| 10.0 | 0.72 | 100 | " | 130 | 8 | 79 |
| 10.0 | 4.80 | 200 | " | 130 | 7 | 74 |
| 10.0 | 100.0 | 190 | " | 130 | 8 | 69 |
| 5.0 | 0.95 | 90 | xylene:DMF 4:1 | 142 | 15 | 55 |
| 20.0 | 2.30 | 90 | toluene:DMF 4:1 | 100 | 120 | 69 |
| 100.0 | 0.94 | 90 | DMSO | 90–100 | 55 | 63 |
| o-iodoaniline·HCl (NH₃Cl) | | | | | | |
| 5.0 | 0.91 | 90 | DMF | 100–110 | 25 | 51 |
| Et₃NHCl 114.0 | 0.96 | 90 | " | 135 | 25 | 61 |
| NH₄Cl | 0.99 | 90 | " | 130–133 | 15 | b |

I claim:

1. A process for preparing a compound of the formula: